US012611515B1

(12) United States Patent

Alcalde et al.

(10) Patent No.: US 12,611,515 B1

(45) Date of Patent: Apr. 28, 2026

(54) ENDOTRACHEAL TUBE HOLDER

(71) Applicant: Marpac, Inc., Albuquerque, NM (US)

(72) Inventors: Jeff Alcalde, Albuquerque, NM (US); David Mayberry, Rio Rancho, NM (US)

(73) Assignee: MARPAC, INC., Albuquerque, NM (US)

( * ) Notice: Subject to any disclaimer, the term of this patent is extended or adjusted under 35 U.S.C. 154(b) by 865 days.

(21) Appl. No.: 17/374,453

(22) Filed: Jul. 13, 2021

Related U.S. Application Data

(60) Provisional application No. 63/051,122, filed on Jul. 13, 2020.

(51) Int. Cl.
*A61M 16/04* (2006.01)
*A61M 16/00* (2006.01)

(52) U.S. Cl.
CPC .... *A61M 16/0497* (2013.01); *A61M 16/0003* (2014.02); *A61M 16/0461* (2013.01); *A61M 16/0475* (2014.02); *A61M 2205/3368* (2013.01); *A61M 2209/088* (2013.01)

(58) Field of Classification Search
CPC .......... A61M 16/0497; A61M 16/0003; A61M 16/0461; A61M 16/0475; A61M 2205/3368; A61M 2209/088
See application file for complete search history.

(56) References Cited

U.S. PATENT DOCUMENTS

| | | | |
|---|---|---|---|
| 1,845,460 A | 2/1932 | Watters | |
| 3,602,227 A | 8/1971 | Andrew | |
| 3,760,811 A | 9/1973 | Andrew | |
| 3,774,616 A | 11/1973 | White et al. | |
| 3,827,433 A | 8/1974 | Shannon | |
| 3,924,636 A | * 12/1975 | Addison ........... | A61M 16/0488 |
| | | | 128/207.14 |
| 4,191,180 A | 3/1980 | Colley et al. | |
| 4,326,515 A | 4/1982 | Shaffer et al. | |

(Continued)

FOREIGN PATENT DOCUMENTS

| | | |
|---|---|---|
| CA | 2166447 | 9/1999 |
| CN | 111249591 A * | 6/2020 |

(Continued)

OTHER PUBLICATIONS

CN-111249591-A description translation accessed May 7, 2024 (Year: 2024).*

(Continued)

*Primary Examiner* — Bradley H Philips
*Assistant Examiner* — Kira B Daher
(74) *Attorney, Agent, or Firm* — Kameron W. Kramer

(57) ABSTRACT

An endotracheal ("ET") tube holder which securely holds the ET tube and enables a healthcare provider to quickly and easily move the ET tube laterally at various positions. The ET tube can be secured to a carriage that slides laterally and can optionally be stopped at one or more predetermined locations, which predetermined locations can optionally be noted with unique identifiers which enable the healthcare provider to accurately document the position of the ET tube. A foam layer is preferably provided to keep rigid plastic components from applying directly contacting and directly applying pressure to the patient's skin.

13 Claims, 9 Drawing Sheets

10

(56) References Cited

U.S. PATENT DOCUMENTS

| | | | |
|---|---|---|---|
| 4,331,143 A | 5/1982 | Foster | |
| 4,378,012 A | 3/1983 | Brown | |
| 4,480,639 A | 11/1984 | Peterson et al. | |
| 4,537,192 A | 8/1985 | Foster | |
| 4,707,906 A | 11/1987 | Posey | |
| 4,744,358 A * | 5/1988 | McGinnis | A61M 16/0497 |
| | | | 128/DIG. 26 |
| 5,009,227 A * | 4/1991 | Nieuwstad | A61M 16/0497 |
| | | | 128/207.14 |
| 5,097,827 A | 3/1992 | Izumi | |
| 5,295,478 A | 3/1994 | Baldwin | |
| 5,345,931 A | 9/1994 | Battagila | |
| 5,437,273 A * | 8/1995 | Bates | A61M 16/0488 |
| | | | 128/207.14 |
| 5,490,504 A * | 2/1996 | Vrona | A61M 16/0488 |
| | | | 128/207.14 |
| 5,558,090 A | 9/1996 | James | |
| 5,643,174 A | 7/1997 | Yamamoto et al. | |
| 5,735,272 A | 4/1998 | Dillon et al. | |
| 5,755,225 A | 5/1998 | Hutson | |
| 6,029,668 A | 2/2000 | Freed | |
| 6,067,985 A * | 5/2000 | Islava | A61M 16/0488 |
| | | | 128/207.14 |
| 6,755,191 B2 | 6/2004 | Bertoch et al. | |
| 7,562,658 B2 | 7/2009 | Madaus et al. | |
| 8,302,597 B2 | 11/2012 | Beely et al. | |
| 8,974,382 B2 | 3/2015 | Taljaard | |
| 9,308,340 B2 | 4/2016 | Bond et al. | |
| 10,888,680 B2 | 1/2021 | Zickefoose et al. | |
| 11,318,283 B1 | 5/2022 | Shackelford et al. | |
| 2008/0294117 A1 | 11/2008 | Ware | |
| 2009/0211573 A1 * | 8/2009 | Russo | A61M 16/0488 |
| | | | 128/207.14 |
| 2011/0126839 A1 * | 6/2011 | Levine | A61M 16/0497 |
| | | | 128/207.14 |
| 2011/0240034 A1 * | 10/2011 | Ciccone | A61M 16/0493 |
| | | | 128/207.17 |
| 2012/0168571 A1 | 7/2012 | Bond et al. | |
| 2012/0216803 A1 * | 8/2012 | Trodler | A61M 16/049 |
| | | | 128/200.26 |
| 2012/0227747 A1 | 9/2012 | Levine | |
| 2014/0261462 A1 * | 9/2014 | Visconti | A61C 5/90 |
| | | | 128/861 |
| 2014/0261463 A1 | 9/2014 | Visconti et al. | |
| 2014/0326247 A1 * | 11/2014 | Dirven | A61M 16/0468 |
| | | | 128/207.16 |
| 2016/0271349 A1 * | 9/2016 | Zickefoose | A61M 16/0497 |
| 2016/0339194 A1 | 11/2016 | Molden et al. | |
| 2017/0197049 A1 * | 7/2017 | Doll | A61M 16/0497 |
| 2019/0232004 A1 * | 8/2019 | Conrad | A61M 16/0411 |
| 2019/0388303 A1 | 12/2019 | Sharaiha | |
| 2020/0009342 A1 * | 1/2020 | Drew | A61B 90/57 |
| 2020/0222651 A1 | 7/2020 | Jockel et al. | |
| 2021/0008315 A1 | 1/2021 | Drew et al. | |
| 2021/0128860 A1 | 5/2021 | Van Der Vegt et al. | |
| 2021/0187229 A1 * | 6/2021 | Brar | A61M 16/0493 |

FOREIGN PATENT DOCUMENTS

| | | | |
|---|---|---|---|
| TW | M453491 U | * | 5/2013 |
| WO | 2015127443 A1 | | 8/2015 |

OTHER PUBLICATIONS

Tw M453491 U description translation accessed May 7, 2024 (Year: 2024).*

"AnchorFast Guard", https://www.hollister.com/en/products/critical-care-products/tube-securement/endotracheal-tube-fasteners/anchorfast-guard-oral-endotracheal-tube-fastener, Feb. 23, 2016.

"AnchorFast1", https://web.archive.org/web/20141218213244/www.anchorfast1.com/images/anchorfast.jpg, Dec. 18, 2014.

"Marpac 320, Adjustable ET Tube Holder, Patent Pending", https://www.youtube.com/watch?v=ZgxwPekeiLg, Sep. 8, 2011.

"Photograph", Source unknown, Nov. 3, 2017.

Reichman, E F, "Emergency Medical Procedures", https://accessemergencymedicine.mhmedical.com/Content.aspx?bookid=683&sectionid=45343703, 2017.

* cited by examiner

ENDOTRACHEAL TUBE HOLDER

CROSS-REFERENCE TO RELATED APPLICATIONS

This application claims priority to and the benefit of the filing of U.S. Provisional Patent Application No. 63/051, 122, entitled "Endotracheal Tube Holder", filed on Jul. 13, 2020, and the specification thereof is incorporated herein by reference.

BACKGROUND OF THE INVENTION

Embodiments of the present invention relate to an endotracheal ("ET") tube holder, hereinafter occasionally referred to as a "holder". More particularly, embodiments of the present invention relate to a holder that allows only soft components to contact a patient and which reduces the amount of adhesive that contacts a patient by providing the adhesive on an upper portion of the backing and which further allows for easy lateral adjustment of the ET tube by providing a push-button adjustment with locking detents across a bridge of the holder.

Although ET tubes provide life-saving support for patients in need, the use of such tubes and the necessary ET tube holders that keep the tubes properly positioned, particularly for prolonged periods, can result in ailments and can be cumbersome and difficult to work with, which makes it difficult to keep the ET tube properly positioned on a consistent basis. Often, the weight of the tube and connected devices can pull the tube down, even when the tube is held with an ET tube holder. This can result in hard plastic parts pressing against locations on the patient, which can result in wounds developing at those contact points. In addition, when the tube is pulled down, it can cause the tube holder to become detached or partially detached and can result in the tube being positioned in a less than optimal position.

Typically, known ET tube holders have adhesive applied across the entirety or nearly the entirety of their backing even though the lower portion of the backing is typically in compression against the user's skin. Long-term use of such adhesives can cause the patients skin to break down. There is thus a present need for a holder which can hold an ET tube in a desired location while reducing the amount of adhesive needed to contact a patient and while providing easy lateral adjustment of the ET tube.

BRIEF SUMMARY OF EMBODIMENTS OF THE PRESENT INVENTION

Embodiments of the present invention relate to an endotracheal ("ET") tube holder that includes a neck strap, a track having a bridge portion, the bridge portion having identifiers positioned at predetermined locations along the bridge portion, a carriage that is movably positionable along the bridge portion, and a pad coupled to the track, the track disposed on a front side of the pad. The ET tube holder can also include an adhesive, the adhesive disposed on a back side of the pad. The adhesive can be disposed only on an upper portion of the back side of the pad. The ET tube holder can also include a securing device disposed on the carriage, the securing device configured to secure an ET tube to the carriage. The securing device can include a belt and a clamping buckle disposed on the carriage, the clamping buckle configured to secure the belt. The belt can include one or more holes and the clamping buckle can include a peg configured to engage the one or more holes. The securing device can optionally include a hook and loop fastener.

In one embodiment, the ET tube holder can include an orogastric ("OG") or nasogastric ("NG") tube holder. The OG or NG tube holder can be disposed on the track. A temperature sensor can also be provided and can be positioned to contact patient skin when the ET tube holder is positioned on a patient in the intended operating position. The temperature sensor can include a color changing material. The temperature sensor can be an electrical temperature sensor.

In one embodiment, an actuator can be communicably coupled to the carriage of the ET tube holder. The actuator can optionally be an electrically powered actuator. Optionally, the track can include openings through which the neck strap can be attached. The carriage can include a push button mechanism that enables the carriage to be locked into one or more locations along the bridge.

Embodiments of the present invention also relate to a method for holding an endotracheal ("ET") tube on a patient, which includes securing an ET tube holder to a patient by placing a neck strap around the patient, protecting a face of the patient from contacting a track of the ET tube holder by disposing padding between the track and the patient's face; securing the ET tube to the ET tube holder by wrapping a belt around the ET tube and attaching the belt to a buckle on a carriage of the ET tube holder; and securing the buckle by wrapping a tail of the belt around the ET tube and then securing the belt to the buckle by placing a peg of the buckle through a hole in the belt. Optionally, attaching the belt to a buckle can include wrapping the belt around the ET tube and clamping it into the buckle.

In one embodiment, the method can include noting a location of the ET tube by referencing indicia that is disposed or otherwise formed on a bridge portion of the track. Optionally, securing the ET tube holder to the patient can also include securing the padding to the patient with an adhesive. Securing the padding to the patient with an adhesive can itself include securing only an upper portion of the padding to the patient with the adhesive. Securing the padding to the patient with an adhesive can optionally include protecting a mustache of the patient from contacting the adhesive by covering a portion of the adhesive that is directly in front of the patient with a non-adhesive material.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more embodiments of the invention and are not to be construed as limiting the invention. In the drawings.

DETAILED DESCRIPTION OF THE INVENTION

Figure 1:
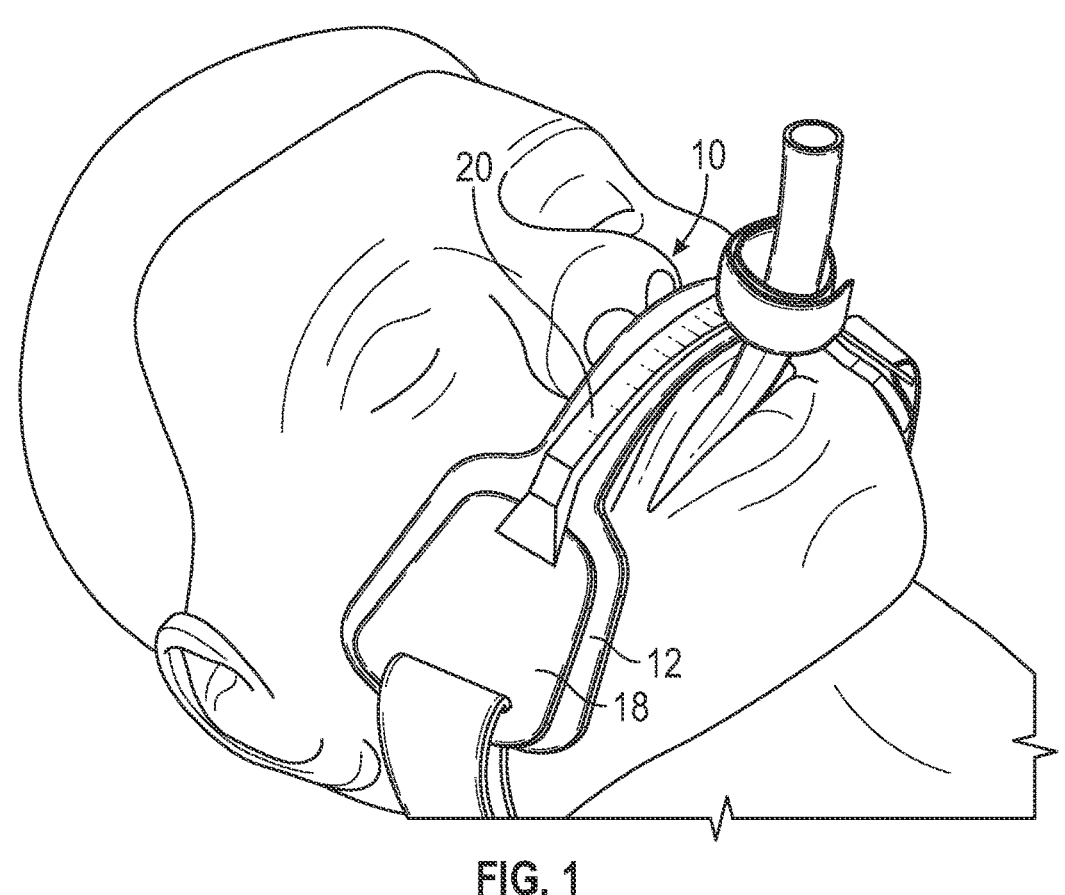
FIG. 1 illustrates the holder attached to a patient while holding an ET tube.

As used throughout this application, the terms "upper" and "lower" are intended to describe an axis that would lie along a primary axis of the patient, when the device is in use in its intended operational configuration. Thus, the term "upper" is in the direction toward the top of the patient's head and "lower" is toward the patient's feet. The terms "front" and "back" are intended to describe an axis that would extend in front of the patient about an axis that is normal with respect to a primary axis of the patient when the device is in use in its intended operational configuration. Thus, the term "back" is intended to mean a location that is closer to a front of the patient and "front" is intended to mean a location that is further in front of the patient. Thus, a "back" of a backing plate describes the surface that could contact a user's face while the "front" of the backing plate describes an opposing surface of the backing plate.

Referring now to the figures, holder 10 preferably includes pad 12 with adhesive 14, which is most preferably a hydrocolloid material, with covering 16 which can be peeled off to expose adhesive 14. Track 18 is most preferably attached to pad 12 so that pad 12 contacts the patient. As best illustrated in FIG. 4C, in one embodiment, non-stick material 50 can be provided to cover a portion of adhesive 14 at a location of a patient's mustache to prevent the mustache from being adhered to adhesive 14. In one embodiment, non-stick material 50 can be a portion of covering 16. In one embodiment, non-stick material 50 can be separate from and/or a different material than covering 16. Thus, in one embodiment, covering 16 can be precut or otherwise perforated to enable a care provider to remove all of covering 16 or only a portion thereof, such that the remaining covering 16 can be left covering adhesive 14 at a location of the patient's mustache or it can also be removed. In one embodiment, pad 12 can extend across the patient's upper lip, or just above the patient's upper lip.

Track 18 can be attached to pad 12 using any known and/or desirable attachment method, including but not limited to one or more of an adhesive, sewing, and/or otherwise imbedding a portion of track 18 into pad 12 (including but not limited to forming pad 12 onto a portion of track 18). Track 18 preferably includes bridge portion 20 which preferably projects away in front of pad 12. Pad 12 is most preferably formed from a soft and flexible material and most preferably underlies all rigid components so that pad 12 protects the patient from coming into contact with any rigid components of holder 10. In one embodiment, pad 12 can be formed from a foam material. In one embodiment, at least a portion of pad 12 is disposed between the patient and track 18 so that track 18 is not placed directly against the patient's skin.

Neck strap 21 most preferably attaches to track 18 through slots 19 disposed near the end portions of track 18. Although neck strap 21 can be attached via any known method, in one embodiment, one or more hook and loop fasteners 23 are preferably attached to end portions of neck strap 21.

Figure 6:
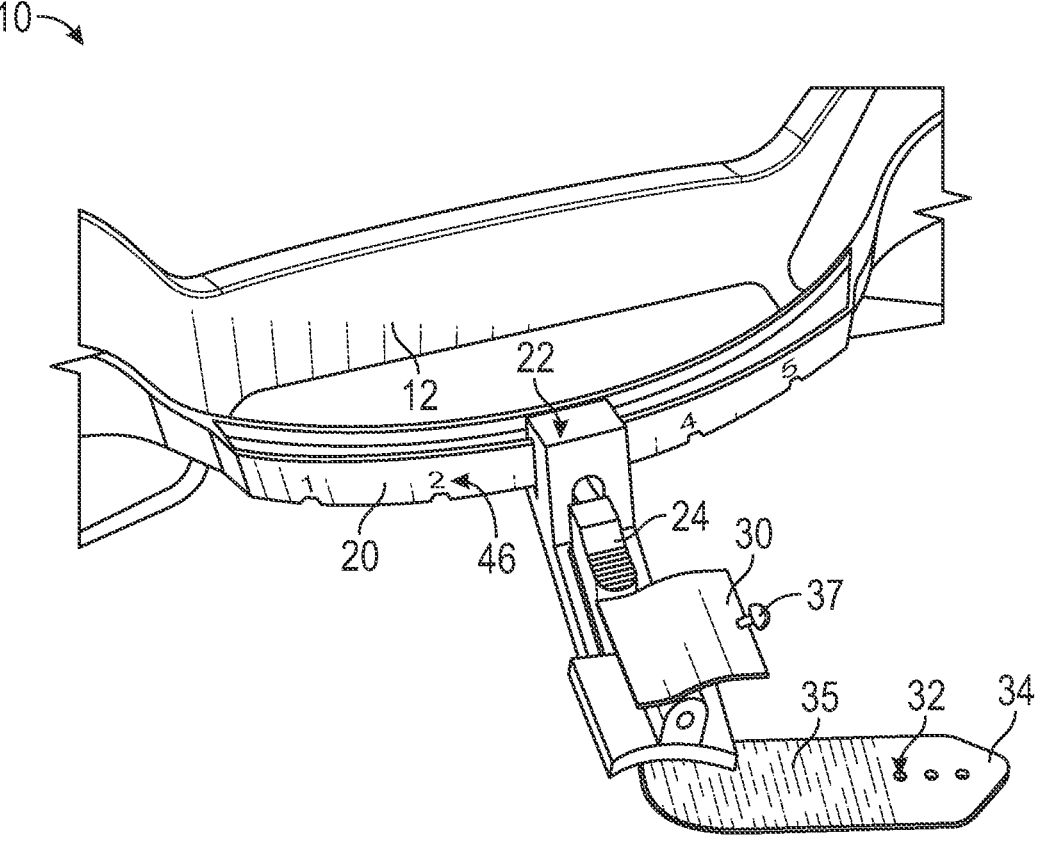
FIG. 6 illustrates a rotatable tube holder buckle and strap of an embodiment of the present invention.
Figure 7A:
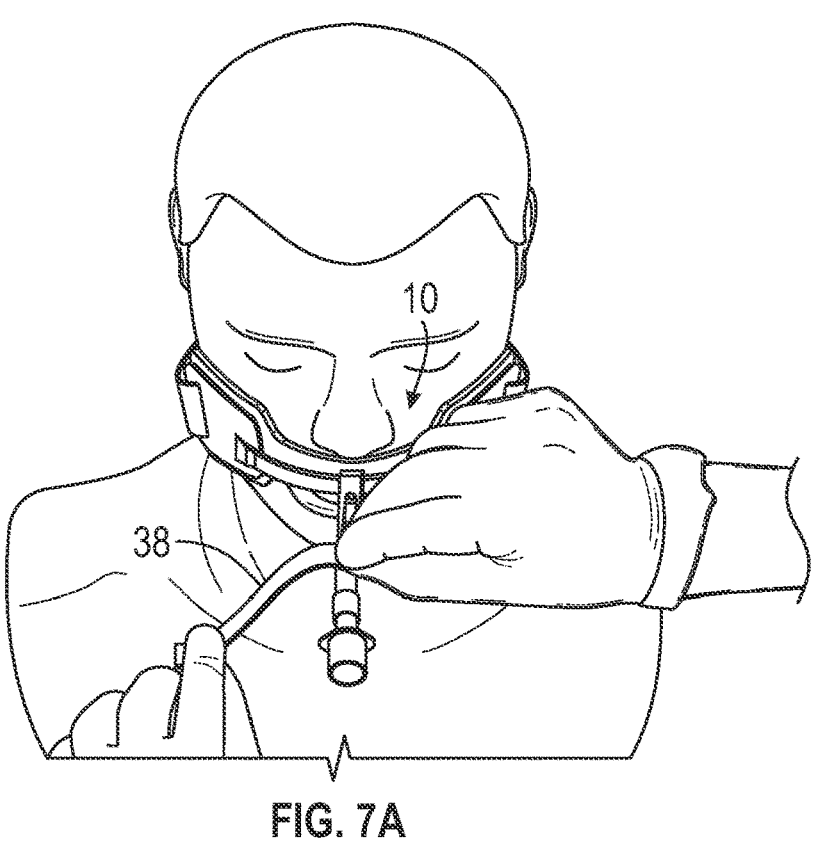
FIGS. 7A and 7B illustrate an optional securing strap around a belt and buckle of the holder.
Figure 7B:
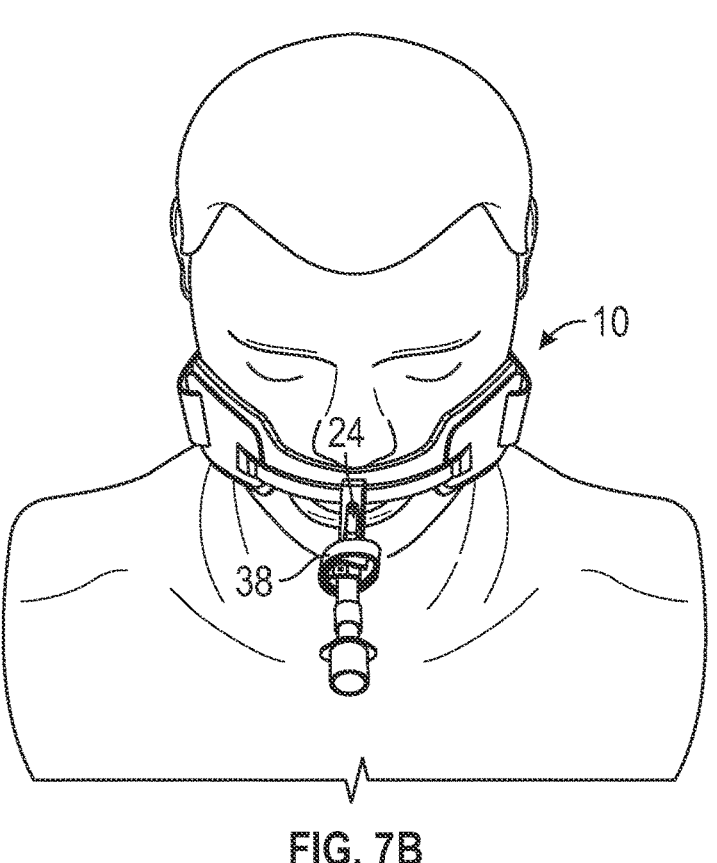
Figure 8:
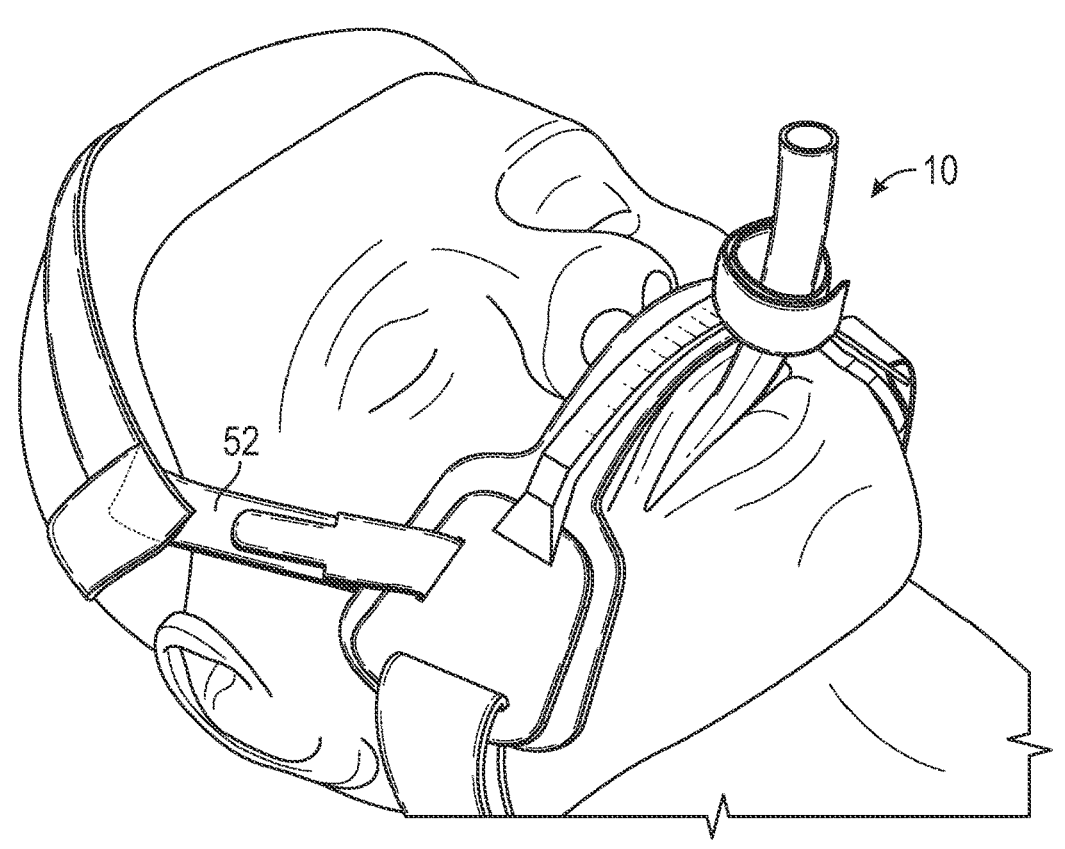
FIG. 8 is a drawing which illustrates an embodiment wherein a head strap is provided.

Carriage 22 is most preferably configured to translate across bridge portion 20 of track 18 while holding an ET tube. Carriage 22 preferably includes push button 24 which is communicably coupled to tongue 26 (see FIG. 5) such that tongue 26 can lock into and be removed from locking detents 28 that are preferably placed at predetermined locations along track 18. Most preferably about 5 locations can be provided with locking detents 28, but optionally, more or fewer locations can be provided. Thus, carriage 22 can be translated about bridge portion 20 and locked into place via tongue 26 and locking detents 28. This enables an ET tube to be translated to different placement positions with respect to a patient which is highly desirable, particularly for patients who require an ET tube for extended durations. Accordingly, embodiments of the present invention can be used for extended periods of time including consecutive days of use. By providing locking detents at a plurality of locations, the exact placement and/or change in placement of an ET tube location can easily be known and achieved. In one embodiment, each detent location can be provided with location identifier 46 (see FIG. 6), which can include for example numbers, letters, or other indicia. For example, as illustrated in FIG. 6, each stop can have unique numbers 1 through 5 for each of the 5 stops, which identifiers can optionally be molded, stamped, printed or otherwise formed or disposed on bridge portion 20 of track 18. This allows for documentation and/or prescription of the exact location of where the tube is, should be, or was disposed. For example, a provider can document that the ET tube was at location 2 on a particular date and was moved to location 5 on a particular date at a particular time.

Figure 4A:
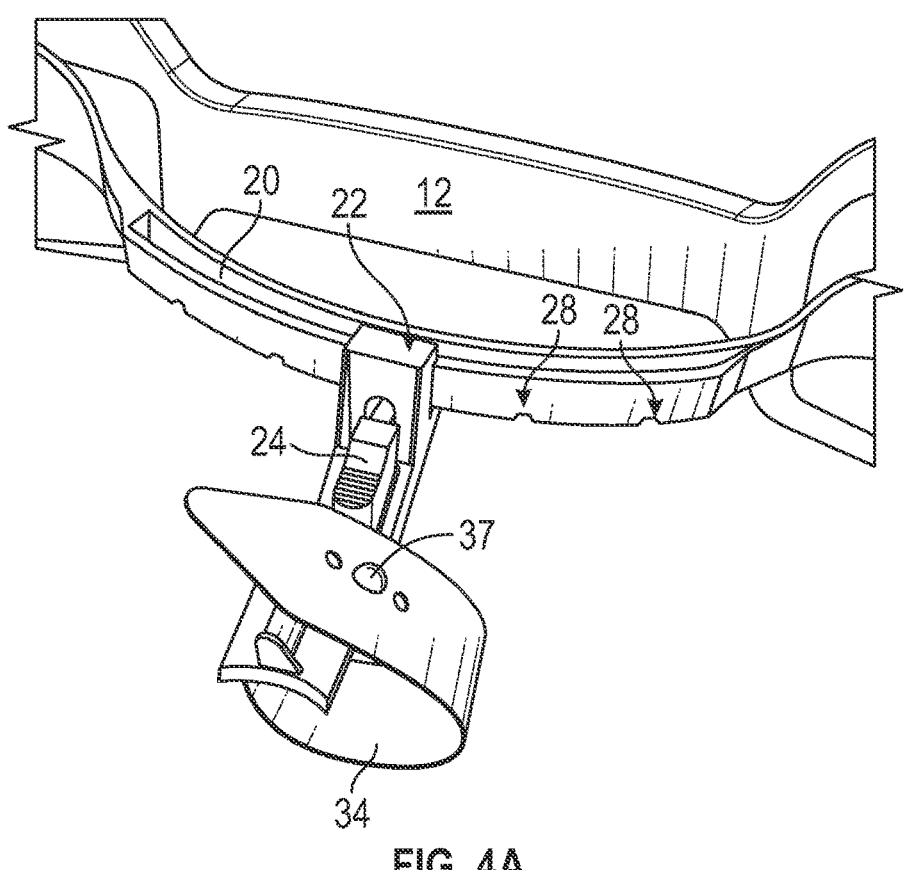
FIGS. 4A and 4B illustrate a movable carriage attached to a track on a bridge of an ET tube holder according to an embodiment of the present invention.
Figure 4B:
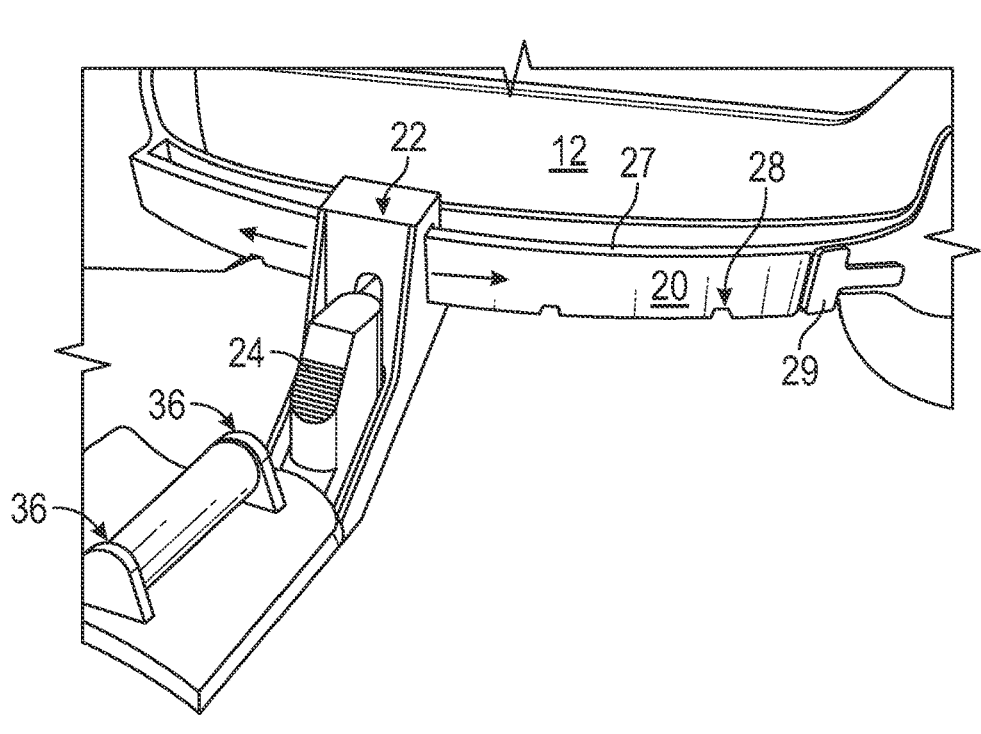
Figures 4C, 5:
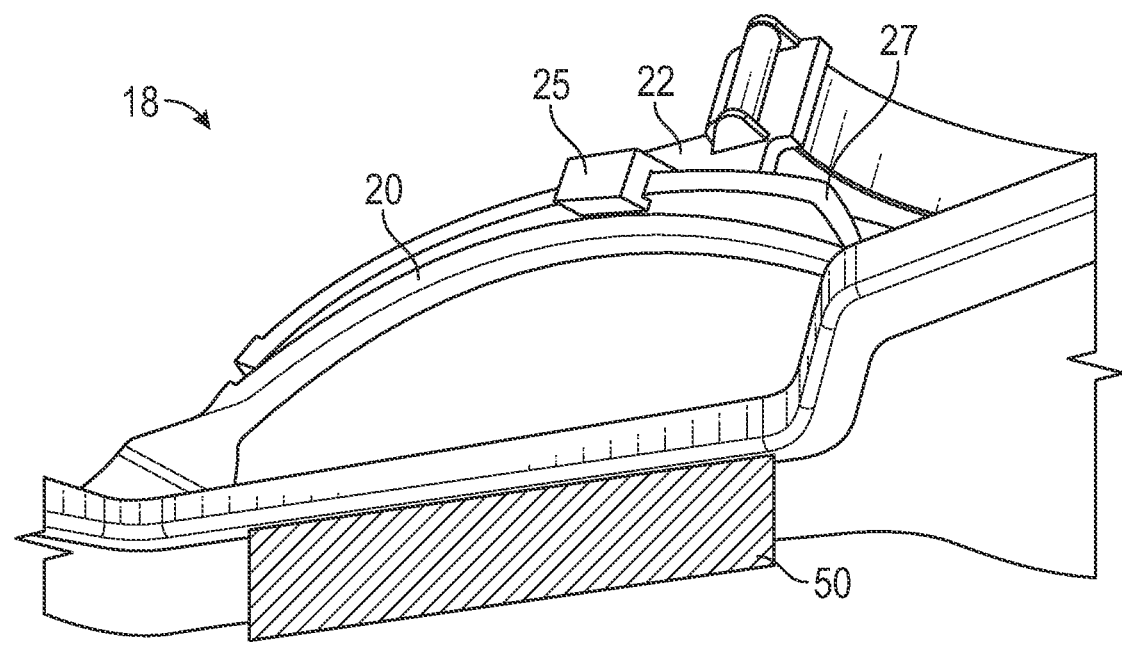
FIG. 4C illustrates a view of a bottom of a carriage disposed in a track of a bridge of an ET tube holder according to an embodiment of the present invention.
FIG. 5 illustrates an underside of a carriage such that an engaging tongue of the carriage is visible.

As best illustrated in FIG. 4B, stop 29 is preferably formed into or onto bridge portion 20 of track 18 which is most preferably configured to allow carriage to be slid onto bridge portion 20 of track 18, but which prevents carriage from then inadvertently sliding off of bridge portion 20.

Although any configuration of push button 24 can be provided which enables tongue 26 to engage and/or disengage with one or more locking detents 28, in one embodiment, push button 24 is preferably resiliently connected to or incorporated into carriage 22 such that after depressing push button 24 it returns to its original position. In one embodiment, push button 24 is most preferably molded as a component of carriage 22.

As best illustrated in FIG. 4C, carriage 22 most preferably comprises track-engaging portion 25 which engages on rail 27 of track 18. Rail 27 is most preferably disposed on bridge portion 20 of track 18. In one embodiment, if additional support is desired, head strap 52 can be provided on holder 10. In this embodiment, head strap 52 can optionally be attached to track 18 or to any other portion of holder 10 which is desirable. The head strap can help support holder 10 in a position that resists sagging or pulling due to the pull by the ET tube and any connected ventilator equipment.

Although track-engaging portion 25 is illustrated as a C-shape which slides about rail 27, other shapes can be used and will provide desirable results. Thus, track-engaging portion 25 and rail 27 are intended to include other shapes which enable a slidable relationship between the two. For example, rail 27 can comprise a channel and track-engaging portion 25 can comprise a tab that slides in such channel.

Buckle 30 is most preferably rotatably connected to carriage 22 via one or more hinges or pivot points 36 (see FIG. 4B). This pivoting of buckle 30 enables a first pass of belt 34 to pass under a bottom portion of buckle 30 such that when buckle 30 is secured to belt 34, buckle 30 cams down to clamp down and pinch the portion of belt 34 that passes beneath it, thus holding belt 34 securely in place. Most preferably, buckle 30 is configured such that simply by passing a portion of belt 34 under buckle 30 and then clamping buckle 30 down to pinch belt 34 (for example, the clamping buckle can comprise a cam-locking buckle), belt 34 can be held in place even without passing peg 37 of buckle 30 through an opening 32 in belt 34. However, as a backup, buckle 30 not only clamps down on belt 34, but belt 34 most preferably wraps around a tube for a second time and is thereafter secured a second time by passing peg 37 of buckle 34 through an opening 32 in belt 34. This prevents buckle 30 from inadvertently hinging up and thus releasing belt 34. The term "peg" is intended to include any structure capable of passing at least partially through opening 32 to secure belt 34.

Although belt 34 and buckle 30 can securely hold the ET tube, in one embodiment, a securing strap 38 can optionally be placed around belt 34 and buckle 30 after the ET tube has been secured therewith to prevent inadvertent unbuckling of belt 34 and buckle 30. Although securing strap 38 can be formed from any desirable material, in one embodiment, securing strap 38 can include a hook and loop material which can removably adhere a portion of strap 38 to itself. Buckle 30 and belt 34 are most preferably configured such that a care provider can loosen belt 34 from an ET tube with a simple one-handed operation. In one embodiment, belt 34 can optionally include a grip-enhancing material applied to a side of it—for example, belt 34 can include adhesive 35 (see FIG. 6), which can comprise a sticky material (including for example, a pressure sensitive adhesive), which is preferably disposed on one side of belt 34 such that adhesive 35 contacts the ET tube when belt 34 is wrapped around the ET tube, thus helping belt 34 to securely hold the ET tube and reducing or eliminating the possibility of belt 34 slipping down or up the ET tube. Optionally, adhesive 35 can be a substance that is applied to a side of belt 34 or a material that is attached to belt 34.

Most preferably, buckle 30, as best illustrated in FIG. 6, is configured to engage in openings 32 in belt 34 such that belt 34 can be wrapped at least partially around an ET tube, and buckled in place with buckle 30, thus holding the ET tube to carriage 22. Openings 32 can be disposed in belt 34 in any desired location, pattern or configuration to permit numerous adjustments for the tension and positioning of belt 34 on an ET tube. By providing a series of openings along a length of belt 34, holder 10 is able to hold multiple sizes of ET tubes at any prescribed depth while enabling the depth to be easily changed.

Figure 2A:
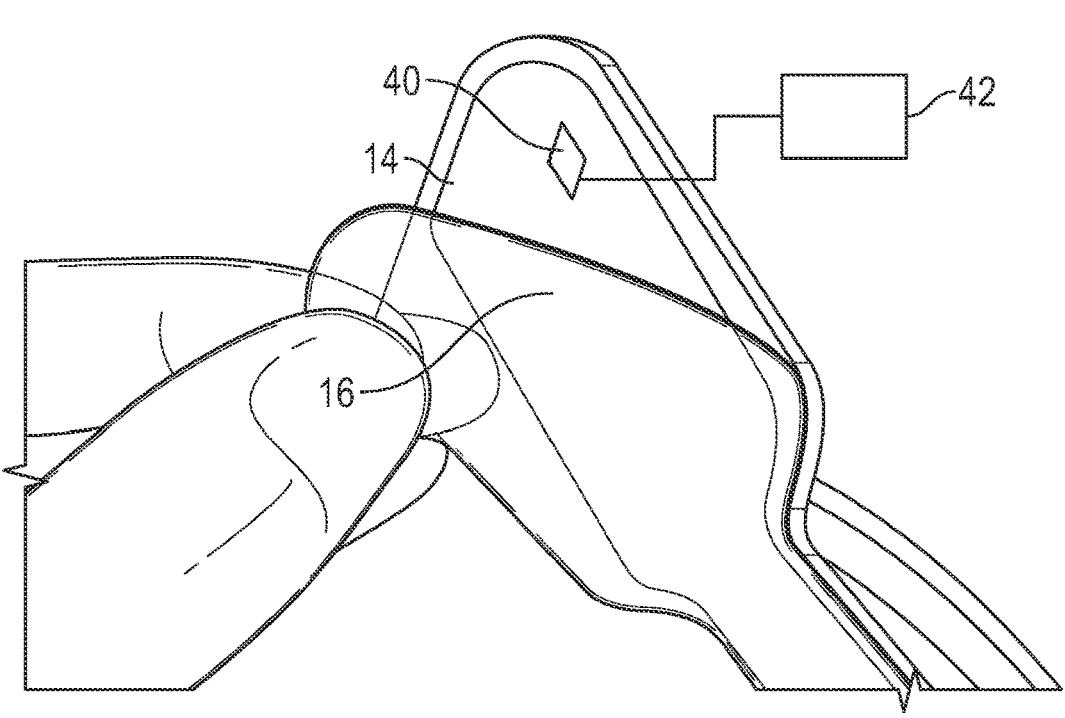
FIG. 2A illustrates an adhesive disposed on a back of a pad with a covering being peeled off.
Figure 2B:
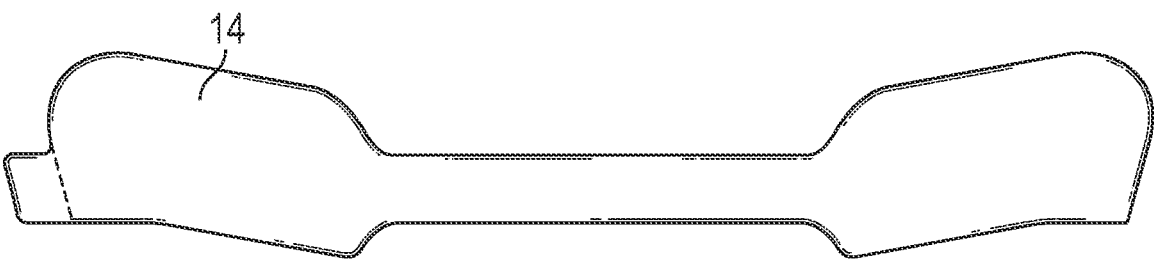
FIGS. 2B, 2C, and 2D respectively illustrate an adhesive with protective covering; a pad, and a neck strap according to an embodiment of the present invention.
Figure 2C:
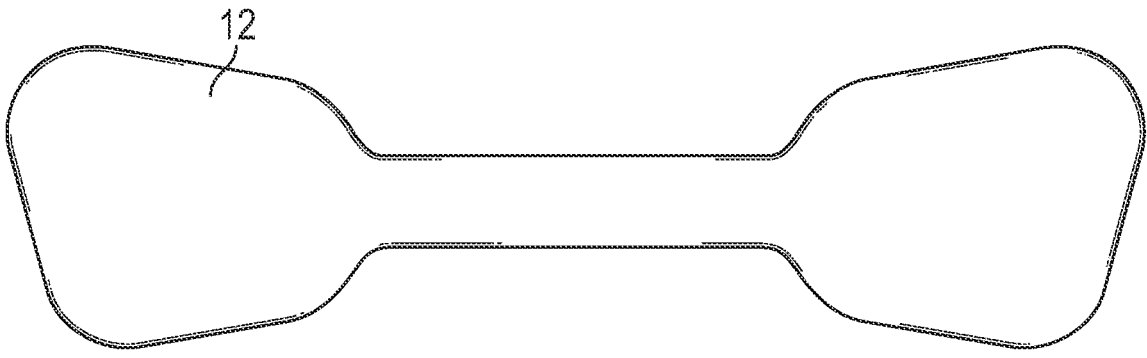
Figure 2D:
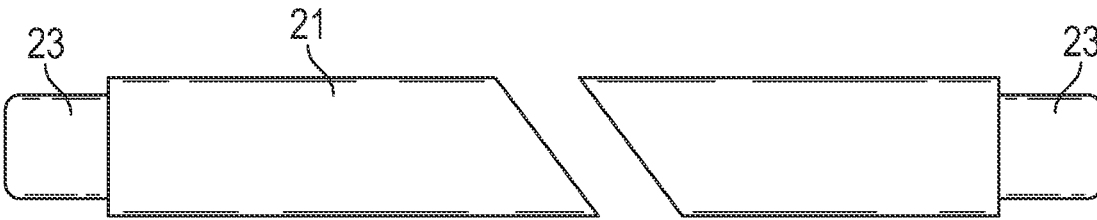

As best illustrated by comparing the shape of adhesive 14 of FIG. 2B to the shape of pad 12 of FIG. 2C, most preferably adhesive 14 is primarily disposed on a top half of pad 12. This is because the lower portion of pad 12 will typically be in compression against the patient's face and thus adhesive on that lower portion does little to effect holding of holder 10 to the user. Thus, in one embodiment, adhesive 14 is not disposed on the lower 10% of pad 12 and more preferably adhesive 14 is not disposed on the lower 25% of pad 12.

Figure 3A:
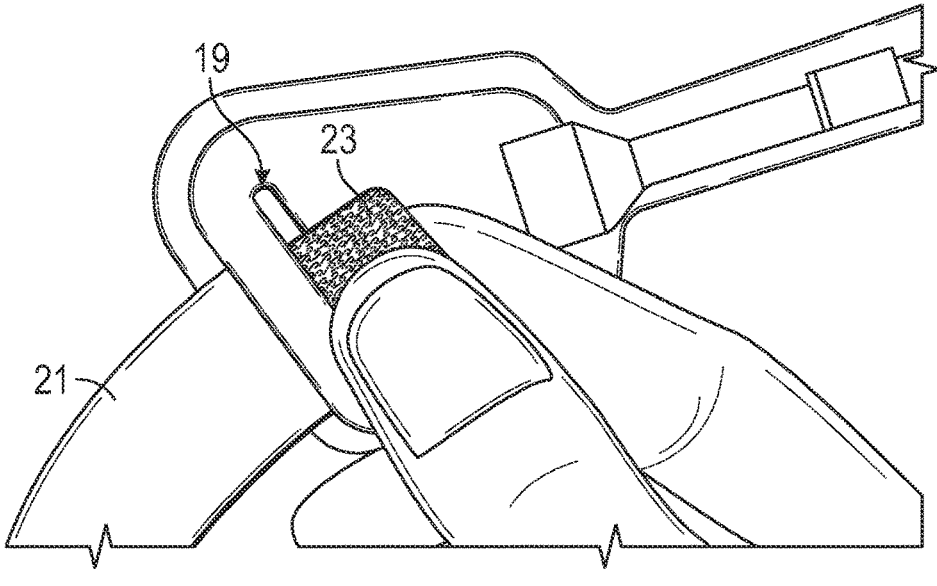
FIGS. 3A and 3B respectively illustrate a close-up detail view and a perspective view of a neck strap being attached according to an embodiment of the present invention.
Figure 3B:
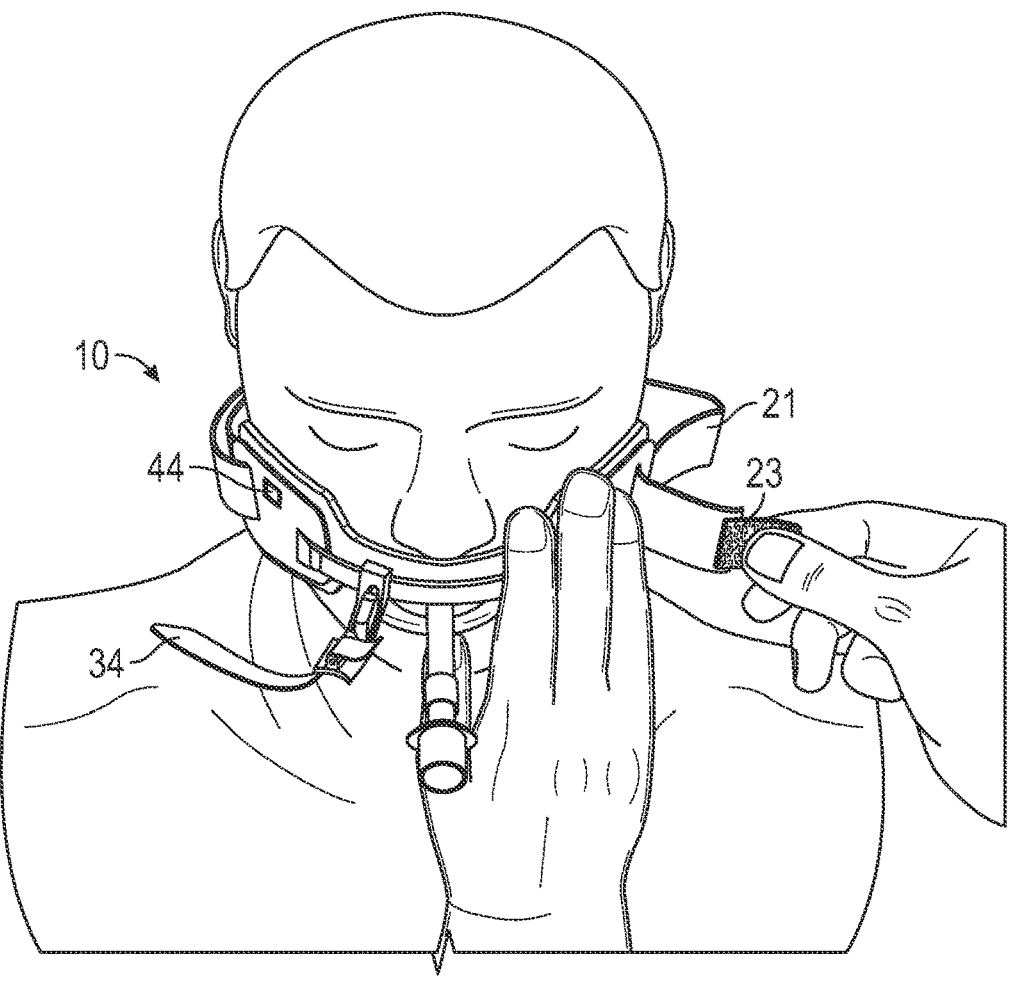

In one embodiment, as best illustrated in FIGS. 2A and 3B, temperature sensor 40 can be disposed in, around, or on adhesive 14. Temperature sensor 40 is preferably configured to detect a temperature rise in a patient's skin at or near a location of contact between the skin and adhesive 14 such that sensor 40 can detect a temperature rise, which may occur when a patient's skin becomes irritated or otherwise begins to break down due to contact with adhesive 14. Optionally, temperature sensor 40 can be configured to detect when a patient's skin reaches a predetermined threshold or which is otherwise outside of a predetermined range of temperatures. This can be desirable for alerting healthcare providers to a possible degradation and/or breakdown in skin tissue that is in contact with adhesive 14.

In one embodiment, sensor 40 can be an electrical sensor and can be coupled to circuit 42 which provides indicia of a rise in temperature—for example, by displaying a visual indicia and/or by sounding an audible indicia (for example, by illuminating a light emitting diode ("LED") and/or by sounding an alarm). In one embodiment, however, temperature sensor 40 can be a color-changing material which changes its color in response to a change in temperature. In this embodiment, opening 44 can be provided in pad 12 and/or in track 18 at a location directly above temperature sensor 40, such that the color change of temperature sensor 40 can be observed by a health care provider.

In one embodiment, to install holder 10 to a patient and secure an ET tube thereto, the following steps are most preferably performed:

1. Insert neck strap 21 into one side of track 18;
2. Remove adhesive covering 16 by pulling an end tab thereof on the back of pad 12;
3. Place pad 12 (with track 18 attached) on the patient's upper lip and cheeks allowing adhesive 14 to adhere to the patient;
4. Slide neck strap 21 under the patient's neck and tighten the other side of neck strap 21;
5. Loop belt 34 around the ET tube and through buckle 30;
6. Pulling belt 34 tight, flip buckle 30 to the closed position; and
7. Wrap belt 34 around the ET tube a second time and align peg on buckle 30 into an opening 32 for secondary securement.

Figure 10:
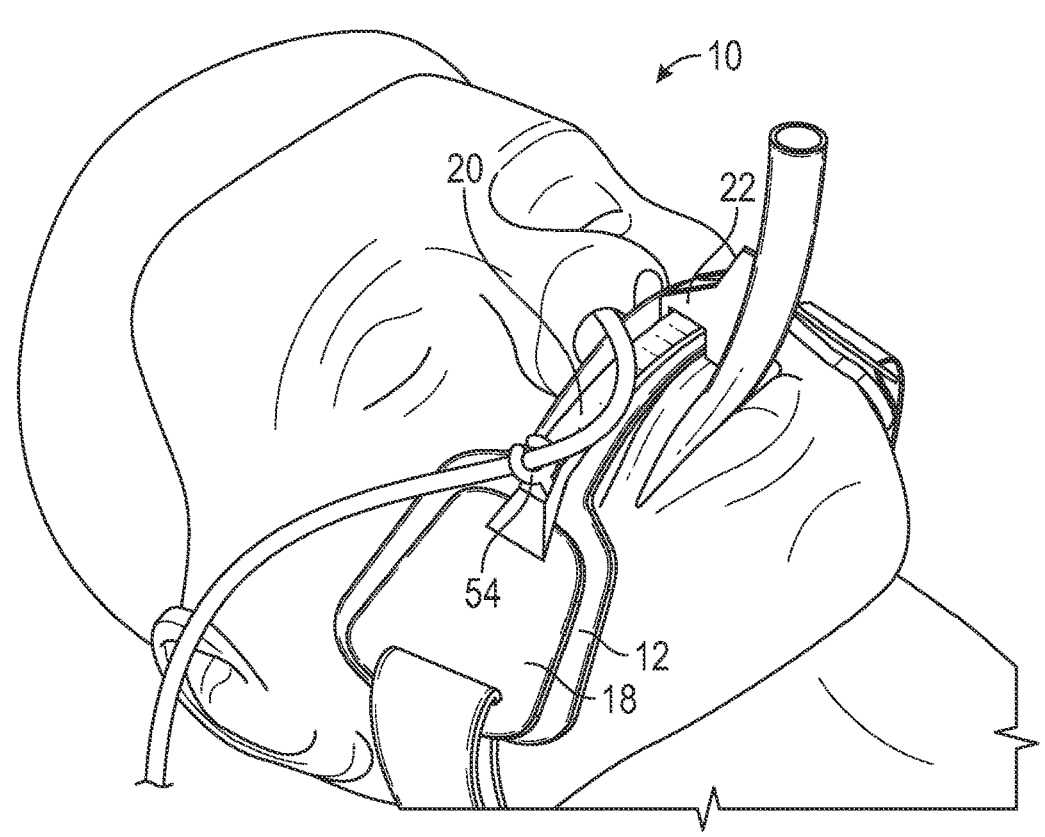
FIG. 10 is a drawing which illustrates an embodiment wherein an orogastric ("OG") tube holder is provided on the ET tube holder according to an embodiment of the present invention.

In one embodiment, carriage 22 can include a clip and/or a second belt which can hold a nasogastric ("NG") or orogastric ("OG") tube while also holding the ET tube. Optionally, the second belt can be secured in any known manner, including with a second buckle, and/or can be self-securing to the second belt (for example, the second belt can be formed from or include a portion of hook and loop material). In one embodiment, as best illustrated in FIG. 10, NG tube holder 54 (which can optionally be used to hold an OG tube) can be provided on track 18 (which can optionally include bridge 20), and not on carriage 22. NG tube holder 54 can comprise a ring, partial ring and/or clip that can hold or otherwise act as a guide for the NG tube.

Figure 9:
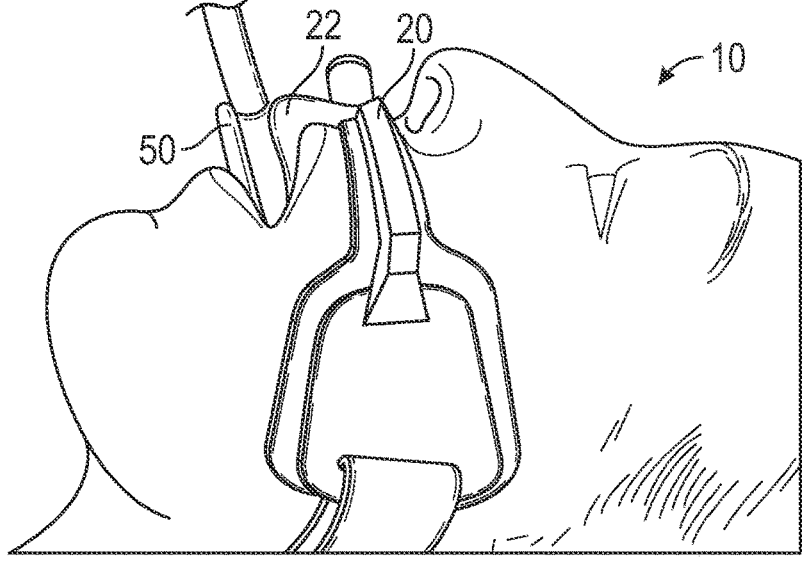
FIG. 9 is a drawing which illustrates a bite guard to prevent a patient from biting the ET tube.

As best illustrated in FIG. 9, in one embodiment, bite guard 50 can be provided on or otherwise coupled to holder 10. Bite guard 50 preferably comprises a rigid structure which protects the ET tube where it enters the patient's mouth and thus prevents the patient from biting and thus collapsing or otherwise damaging the ET tube. In one embodiment, bite guard 50 can comprise an extension of material of carriage 22.

Figure 11:
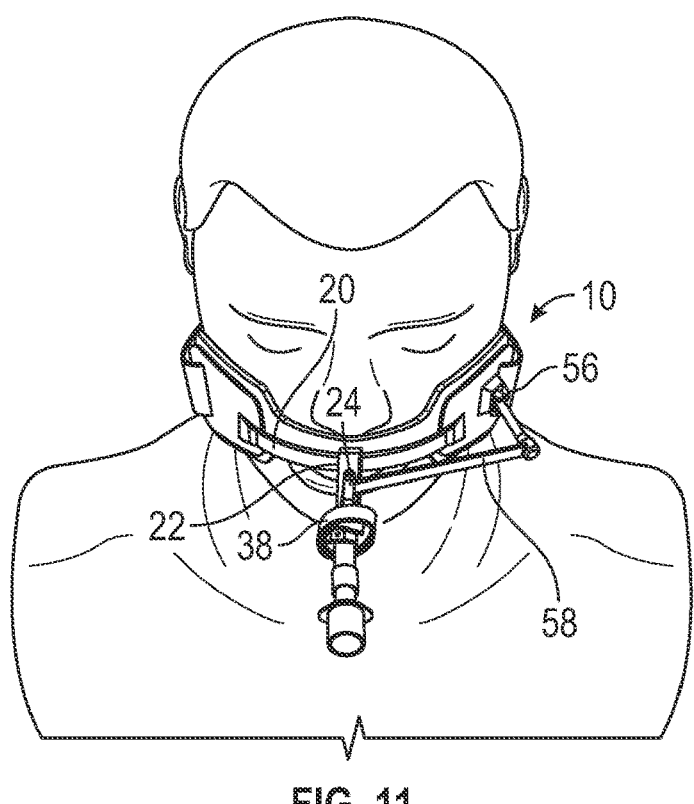
FIG. 11 is a drawing which illustrates an embodiment of the present invention wherein an actuator is provided to move the ET tube laterally with respect to the patient.

Referring now to FIG. 11, in one embodiment, actuator 56, which can comprise an electric motor or other electrically-powered actuator, can be communicably coupled to carriage 22 such that carriage 22 can be moved laterally on bridge portion 20 of track 18. Optionally, one or more pivoting linkages 58 can be provided to couple actuator 56 to carriage 22. Actuator 56 can optionally be activated at predetermined or preprogrammed intervals. For example, in one embodiment, carriage 22 can comprise an opening with female threads disposed therein and a worm gear can be attached with its primary axis substantially parallel with a primary axis of track 18 such that rotation of the worm gear causes carriage 22 to be pushed and/or pulled laterally. In one embodiment, when actuator 56 is provided, detents 28 in track 18 are optionally not provided. Instead, actuator 56 can optionally be activated and caused to stop such that carriage 22 stops at any desired location, including but not limited to predetermined stop locations.

Note that in the specification and claims, "about" or "approximately" means within twenty percent (20%) of the amount or value given.

Embodiments of the present invention can include every combination of features that are disclosed herein independently from each other. Although the invention has been described in detail with particular reference to the disclosed embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference. Unless specifically stated as being "essential" above, none of the various components or the interrelationship thereof are essential to the operation of the invention. Rather, desirable results can be achieved by substituting various components and/or reconfiguring their relationships with one another.

What is claimed is:

1. An endotracheal ("ET") tube holder comprising:
a neck strap;
a track comprising a bridge portion, said bridge portion comprising identifiers positioned at predetermined locations along said bridge portion,
wherein said track comprises openings through which said neck strap is attached;
a carriage, said carriage movably positionable along said bridge portion,
wherein a stop is disposed on said bridge portion that prevents the carriage from sliding off of the bridge portion,
wherein a securing device to secure an ET tube is disposed on said carriage, wherein the securing device comprises a belt and a clamping buckle disposed on said carriage, said clamping buckle configured to secure said belt; and
a pad coupled to said track, said track disposed on a front side of said pad,
wherein said pad is shaped to fit snugly against a patient's face extending from one cheek to the other cheek and on patient's upper lip,
wherein said bridge portion is connected to the pad at the bridge portion's end points and projects away from the pad,
wherein there is separation between the pad and the bridge portion such that the carriage is not in contact with the pad when the carriage is disposed on the bridge portion, and
wherein said carriage comprises a push button mechanism that is communicably coupled to a tongue such that the tongue can lock into and be removed from locking detents disposed on the bridge portion which enables said carriage to be locked into one or more locations along said bridge portion.

2. The ET tube holder of claim 1 wherein said belt comprises one or more holes and wherein said clamping buckle further comprises a peg configured to engage said one or more holes.

3. The ET tube holder of claim 1 wherein said securing device further comprises a hook and loop fastener.

4. The ET tube holder of claim 1 further comprising an adhesive, said adhesive disposed on a back side of said pad.

5. The ET tube holder of claim 4 wherein said adhesive is disposed only on an upper portion of said back side of said pad.

6. The ET tube holder of claim 1 further comprising an orogastric ("OG") or nasogastric ("NG") tube holder.

7. The ET tube holder of claim 6 wherein said OG or NG tube holder is disposed on said track.

8. The ET tube holder of claim 1 further comprising an actuator communicably coupled to said carriage.

9. The ET tube holder of claim 8 wherein said actuator is an electrically powered actuator.

10. The ET tube holder of claim 1 further comprising a temperature sensor positioned to contact patient skin when said ET tube holder is positioned on a patient in the intended operating position.

11. The ET tube holder of claim 10 wherein said temperature sensor comprises a color changing material.

12. The ET tube holder of claim 10 wherein said temperature sensor comprises an electrical temperature sensor.

13. An endotracheal ("ET") tube holder comprising:
a neck strap;
a head strap;
a track comprising a bridge portion, said bridge portion comprising identifiers positioned at predetermined locations along said bridge portion;
a carriage, said carriage movably positionable along said bridge portion; and
a pad coupled to said track, said track disposed on a front side of said pad,
wherein said pad is shaped to fit snugly against a patient's face extending from one cheek to the other cheek and on patient's upper lip,
wherein said track comprises openings through which said neck strap and head strap are attached, and
wherein the bridge portion is connected to the pad at the bridge portion's end points and projects away from the pad wherein there is separation between the pad and the bridge portion such that the carriage is not in contact with the pad when the carriage is disposed on the bridge portion.

\* \* \* \* \*